United States Patent [19]

Hofmeister et al.

[11] Patent Number: 4,945,064
[45] Date of Patent: Jul. 31, 1990

[54] ESTRANE AND ANDROSTANE DERIVATIVES, PROCESS FOR PRODUCING THEM AND PREPARATIONS CONTAINING THESE COMPOUNDS

[75] Inventors: Helmut Hofmeister; Henry Laurent; Paul E. Schulze, all of Berlin; Klaus Annen, Muenster-Albachten; Rudolf Wiechert, Berlin; Kunhard Pollow, Mainz-Hechtsheim; Bernhard Manz, Mains-Bretzenheim; Hans-Joerg Grill, Mainz, all of Fed. Rep. of Germany

[73] Assignee: Schering Aktiengesellschaft, Berlin and Bergkamen, Fed. Rep. of Germany

[21] Appl. No.: 147,580

[22] Filed: Jan. 19, 1988

Related U.S. Application Data

[63] Continuation of Ser. No. 737,242, Dec. 3, 1986, abandoned, which is a continuation of Ser. No. 659,581, Oct. 10, 1984, abandoned.

[30] Foreign Application Priority Data

Oct. 10, 1983 [DE] Fed. Rep. of Germany ....... 3337179

[51] Int. Cl.$^5$ ............... G01N 33/566; G01N 33/567; C07J 1/00; C07J 3/00
[52] U.S. Cl. .................................... 436/503; 436/501; 436/504; 424/1.1; 514/169; 514/178; 552/504; 552/526; 552/650; 552/639; 552/648; 552/510; 540/3; 540/15; 540/40
[58] Field of Search ........................ 436/501, 503, 504; 514/169, 178; 260/397.4, 397.5; 424/1.1

[56] References Cited

U.S. PATENT DOCUMENTS 3,498,975  3/1970  Oberster et al. ................. 260/397.4
4,321,208  3/1982  Sahadevan ................. 260/397.45 X
4,541,957  9/1985  Nakutsuka et al. .............. 260/397.5

OTHER PUBLICATIONS

Pichon, M. et al. Cancer Res. 37:464–471, (1977).
Hanson, R., et al., Jour. Nucl. Med., 23:431–436, (1982).

Primary Examiner—Jack Spiegel
Attorney, Agent, or Firm—Millen, White & Zelano

[57] ABSTRACT

Estrane and androstane derivatives of formula I

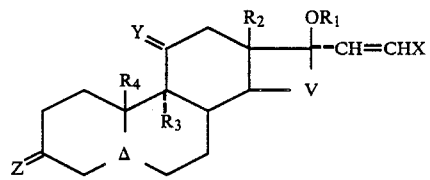

wherein
X is bromine, iodine, triphenyltin or trialkyltin of 1 to 6 carbon atoms per alkyl radical,
Y represents two hydrogen atoms or methylene,
Z represents two hydrogen atoms, oxo or alkylenedioxy of 2 to 6 carbon atoms and
V is ethylene, vinylene, 1,3-propylene or cyclopropylene,
$R_1$ is hydrogen or a hydrocarbon radical of up to 8 hydrocarbon atoms, optionally interrupted by an oxa group or substituted by an oxo group,
$R_2$ is methyl or ethyl,
$R_3$ and $R_4$ represent a carbon-carbon bond or $R_3$ is hydrogen and $R_4$ is hydrogen or methyl,
$\Delta$ symbolizes a 4(5)-double bond if Z signifies two hydrogen atoms or an oxo group; or a 5(6)-double bond or, for the estrane derivatives of formula I, also a 5(10)-double bond, if Z is alkylenedioxy, are pharmacologically effective substances or intermediates for preparation thereof.

38 Claims, No Drawings

ESTRANE AND ANDROSTANE DERIVATIVES, PROCESS FOR PRODUCING THEM AND PREPARATIONS CONTAINING THESE COMPOUNDS

This application is a continuation of application Ser. No. 937,242, filed Dec. 3, 1986, now abandoned which is a continuation of application Ser. No. 06/659,581, 10/10/84 now abandoned.

This invention relates to new estrane and androstane derivatives.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been attained by providing new estrane and androstane derivatives of formula I

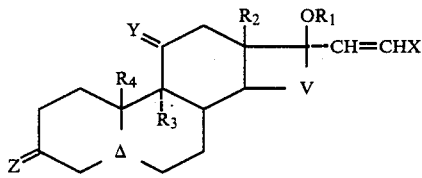

wherein

X is a bromine atom, an iodine atom, a triphenyltin group or a trialkyltin group with 1 to 6 carbon atoms per alkyl radical, Y represents two hydrogen atoms or a methylene group, Z respresents two hydrogen atoms, an oxo group or an alkylenedioxy group with 2 to 6 carbon atoms and V is an ethylene group, a vinylene group, a 1,3-propylene group or a cyclopropylene group, $R_1$ is a hydrogen atom or a hydrocarbon radical, with a maximum of 8 hydrocarbon atoms, optionally interrupted by an oxa group or substituted by an oxo group, and $R_2$ is a methyl or ethyl group, $R_3$ and $R_4$ together represent a carbon-carbon bond or $R_3$ is a hydrogen atom and $R_4$ is a hydrogen atom or a methyl group, and Δ symbolizes a 4(5)-double bond, if Z signifies two hydrogen atoms or an oxo group; or Δ symbolizes a 5(6)-double bond or in the case of the estrane derivatives of formula I also a 5(10)-double bond, if Z signifies an alkylenedioxy group.

DETAILED DISCUSSION

The compounds of formula I can carry as substituents $R_1$ a hydrogen atom or, optionally, a hydrocarbon group, with a maximum of 8 carbon atoms, optionally interrupted by an oxa group or substituted by an oxo group. These radicals include, for example, saturated or unsaturated, cyclic or acyclic hydrocarbon radicals, e.g., alkyl radicals (methyl, ethyl, propyl, isopropyl, tert-butyl, etc.), alkenyl radicals (2-propenyl, etc.), phenylalkyl, e.g., benzyl, acetal or ketal radicals (methoxymethyl, ethoxymethyl, 2-tetrahydrofuranyl, 2-tetrahydropyranyl, etc.), 1-oxoalkyl radicals (formyl, acetyl, propionyl, butyryl, trimethylacetyl, hexanoyl, etc.) or the benzoyl radical.

The tributyltin group is especially suitable as the trialkyltin group for X. Suitable alkyl portions throughout the foregoing definitions include methyl, ethyl, or a propyl, butyl, pentyl, hexyl, heptyl, or octyl group.

Ethylenedioxy, 1,3-propylenedioxy, 2,2-dimethylpropylenedioxy or 2,3-butylenedioxy groups, for example, are suitable alkylenedioxy groups Z.

The compounds of formula I wherein X is a bromine atom or an iodine atom and Z signifies two hydrogen atoms or an oxo group, are pharmacologically effective substances, which show an action profile like the corresponding 17α-ethinyl compounds. Thus, for example the compounds of formula Ia

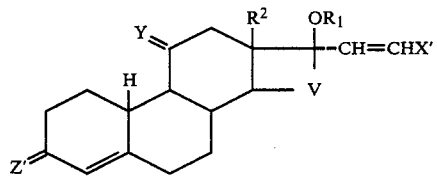

wherein

X' is a bromine atom or an iodine atom

Z' represents two hydrogen atoms or an oxo group, and

V, Y, $R_1$ and $R_2$ are as defined above, have a gestational effectiveness. Thus for example, 17β-hydroxy-17α-(2-iodovinyl)-4-estren-3-one is bonded substantially stronger to the gestagen receptor than norethisterone. In addition, the 9,10-unsubstituted compounds can be used as starting materials for conventional preparation of the corresponding 9,10-hydrogenated steroids.

All of these 17α-halogenvinylsteroid compounds can be administered analogously to their prior art 17α-ethynyl analogs, e.g., in dosages of 0.05 to 250 mg/kg/day, in fully conventional pharmacological formulations.

The compounds of formula I wherein X is a triphenyltin group or a trialkyltin group and/or wherein Z is an alkylenedioxy group are preferred intermediates for production of pharmacologically effective substances.

Production of the estrane and androstane derivatives according to the invention can, for example, be carried out according to a process comprising reacting a compound of formula II

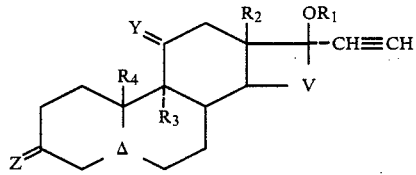

wherein

Y, Z, V, Δ, $R_1$, $R_2$, $R_3$, and $R_4$ are as defined for Formula I with triphenyltin hydride or a trialkyltin hydride of 1 to 6 carbon atoms per alkyl radical, and, optionally, exchanging the organotin radical with bromine or iodine, and, optionally, splitting off a ketal group that is present, e.g., at Z, e.g., by simultaneous isomerization of the double bond.

The reaction of the compound of formula II with triphenyltin hydride or a trialkyltin hydride with 1 to 6 carbon atoms per alkyl radical can be performed in an inert solvent. Suitable solvents, for example, include esters such as diethyl ether, dioxane, tetrahydrofuran, 1,2-dimethoxyethane, dimethylformamide, hexamethylphosphoric triamide, N-methylpyrrolidone, acetonitrile or isopropanol. The reaction can be performed without addition of catalysts or in the presence of radical formers (such as, for example, α,α′-azoisobutyronitrile) as catalyst. If the reaction is performed in the presence of radical formers, it is advantageous to use as the initial compound a 3,3-alkylenedioxy compound or a steroid of formula II unsubstituted in the 3-position, since otherwise there is a danger that the $\Delta^4$-double bond, which is present, will be hydrogenated. If the reaction is performed in the presence of radical formers, the 17α-(E-2-tributylstannylvinyl) compounds of formula I according to the invention are generally formed. Without radical formers, the 17α-(Z-2-tributylstannylvinyl) compounds are generally formed. The reaction is generally conducted at a temperature of 0°–120° C. and a time of 1–100 hours.

The exchange of the triphenyltin group or trialkyltin group for a bromine or iodine atom which optionally follows can be performed in an inert solvent in the presence of agents supplying bromine cations or iodine cations. A suitable method is, for example, the reaction of the organotin compounds in an inert solvent (for example, an ether such as dioxane, tetrahydrofuran or 1,2-dimethoxyethane) with N-bromosuccinimide or N-iodosuccinimide. Other suitable methods include, for example, those described in the publications J. Nucl. Med. 23, 1982, 431, App. Nucl. Radiochem. 1982 or Helv. Chim. Acta, 1982, 1018, which disclosure is fully incorporated by reference herein.

Splitting off the ketal, which follows if desired, is performed fully conventionally with acids (hydrochloric acid, p-toluenesulfonic acid, oxalic acid, formic acid, etc.) in the presence of solvents containing hydroxy groups (water, lower alcohols such as methanol, ethanol, isopropanol) or mixtures of solvents.

The 17α-(2-bromovinyl) and 17α-(2-iodovinyl) steroids of formula I can be used as initial products for the production of the corresponding 17α-(2-radio-halogenvinyl) compounds. Thus 17α-(2-[*I]-iodovinyl) compounds can be produced, by radiochemical methods, from 17α-(2-iodovinyl) or 17α-(2-bromovinyl) steroids by exchange reaction with radioactive sodium-[*I]-iodide in acetone. Analogously, the corresponding 17α-(2-[*Br]-bromovinyl) steroids are formed from 17α-iodo- and 17α-bromovinyl compounds of reaction with radioactive sodium-[*Br]-bromide with addition of copper sulfate. A further method known in the literature for production of 17α-(2-[*I]-iodovinyl) steroids proceeds with the 17α-(2-tributylstannylvinyl) compounds of this invention which are reacted with radioiodine, e.g., [$^{125}$I]I$_2$ (R. N. Hanson et al., J. Nucl. Med. 23, 431 (1982)) which disclosure is incorporated by reference herein).

Suitable radioactive iodine isotopes are, for example, $^{124}$I, $^{125}$I, $^{126}$I or $^{131}$I isotopes; suitable radioactive bromine isotopes are, for example, $^{77}$Br and $^{82}$Br isotopes.

The radioactive compounds thus produced are valuable diagnostic agents. Thus, the compounds of formula Ia, because of their affinity for the progestagen receptor, are suitable in medicine for diagnostic purposes. They can be used as radio-diagnostic agents. They can be used in scintigraphy for visualization of organs and tumors, which contain receptors, which the vinylhalogen steroids have occupied. In regard to organs, for women, e.g., the sexual organs, especially the uterus and mammary glands can be visualized; for men, principally the prostate, accessory sexual organs, hypophysis and mammary glands are involved. Further, the radiohalogenvinyl steroids can be used for detection of tumors and metastases in the tissues of the organs mentioned. The 17α-[$^{125}$I]-iodovinyl compounds are of special interest since they are suitable for in vitro diagnostics. See Hanson, supra.

The starting compounds of Formula II are all known and/or readily conventionally preparable from known or readily conventionally preparable starting materials. See, e.g., J. Amer. Chem. Soc. 76, 1854, 4092; C. A. 87, 1977, 168, 265K and 50, 1956, 945E; Angew. Chem. Int. Ed. Engl. 14, 1975, 417, and J. Amer. Chem. Soc. 82, 1960, 2402.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

17β-Hydroxy-17α-(Z-2-tributylstannylvinyl)-4-estren-3-one 10.0 g of 17α-ethinyl-17β-hydroxy-4-estren-3-one are stirred in 200 ml of tetrahydrofuran with 30 ml of tributyltin hydride at 70° C. After 4 days, the solvent is distilled off and the residue is chromatographed on silica gel with 0–10% ethyl acetate/hexane. 7.5 g of 17β-hydroxy-17α-(Z-2-tributylstannylvinyl)-4-estren-3-one are obtained. Mp 114.2° C.

EXAMPLE 2

17β-Hydroxy-17α-(Z-2-iodovinyl)-4-estren-3-one 355 mg of N-iodosuccinimide are added to 710 mg of 17β-hydroxy-17α-(2-tributylstannylvinyl)-4-estren-3-one in 14 ml of tetrahydrofuran at room temperature. After 15 minutes, the mixture is added to ice/water drop by drop. The precipitated product is filtered off, dissolved in ethyl acetate, washed several times with water and dried with sodium sulfate. After recrystallization of the crude product from acetone/hexane, 520 mg of 17β-hydroxy-17α-(Z-2-iodovinyl)-4-estren-3-one are obtained. Mp 125.1° C. (decomp.).

EXAMPLE 3

17α-(Z-2-Bromovinyl-17β-hydroxy-4-estren-3-one 1.5 g of 17β-hydroxy-17α-(2-tributylstannylvinyl)-4-estren-3-one in 30 ml of tetrahydrofuran are reacted with 530 mg of N-bromosuccinimide at room temperature within 40 minutes. The reaction mixture is stirred into ice/water and the precipitated product worked up as described in example 2. Yield: 770 mg of 17α-(Z-2-bromovinyl)-17β-hydroxy-4-estren-3-one. Mp 124° C. (decomp.).

EXAMPLE 4

17α-Ethinyl-3,3-ethylenedioxy-5 and 5(10)-estren-17β-ol 10 g of 17α-ethinyl-17β-hydroxy-4-estren-3-one in 100 ml Methylene chloride were stirred with 100 ml of ethylene glycol, 30 ml of trimethyl p-formate and 150 mg of p-toluenesulfonic acid. After 5 hours, 2.5 ml of pyridine are added, the solution is considerably concentrated in vacuo and the residue put in ice/water. The precipitated product is aspirated, dissolved in ethyl acetate, washed with water and dried with sodium sulfate. 11.6 g of 17α-ethinyl-3,3-ethylenedioxy-5 and 5(10)-estren-17β-ol are obtained as oil.

EXAMPLE 5

3,3-Ethylenedioxy-17α-(E-2-tributylstannylvinyl)-5 and 5(10)-estren-17α-ol 2.0 g of 17α-ethinyl-3,3-ethylenedioxy-5 and 5(10)-estren-17β-ol are stirred in 40 ml of absolute tetrahydrofuran with 10 ml of n-tributyltin hydride and 400 mg of α,α'-azoisobutyronitrile for 1 hour at 70° C. After cooling, the reaction mixture is diluted with ethyl acetate, washed with water and dried with sodium sulfate. 1.8 g of 3,3-ethylenedioxy-17α-(E-2-tributylstannylvinyl)-5 and 5(10)-estren-17β-ol are isolated as oil after column chromatography on silica gel with 0–10% ethyl acetate/hexane.

EXAMPLE 6

3,3-Ethylenedioxy-17α-(E-2-iodovinyl)-5- and 5(10)-estren-17β-ol 770 mg of N-iodosuccinimide are added to 1.5 g of 3,3-ethylenedioxy-17α-(E-2-tributylstannylvinyl)-5 and 5(10)-estren-17β-ol in 30 ml of abs. tetrahydrofuran at room temperature. After 1 hour, it is diluted with ethyl acetate and dried with sodium sulfate. 800 mg of 3,3-ethylene-dioxy-17α-(E-2-iodovinyl)-5 and 5(10)-estren-17β-ol are obtained after recrystallization from ether/hexane. Mp 172.2° C. (decomp.).

EXAMPLE 7

17α-(E-2-Bromovinyl)-3,3-ethylenedioxy-5 and 5(10)-estren-17β-ol 1.5 g of 3,3-Ethylenedioxy-17α-(E-2-tributylstannylvinyl)-5 and 5(10)-estren-17β-ol, analogously to example 6, are reacted with 540 mg of N-bromosuccinimide and worked up. 700 mg of 17α-(E-2-Bromovinyl-3,3-ethylenedioxy-5 and 5(10)-estren-17β-ol with an Mp of 154.3° C. (decomp.) are obtained.

EXAMPLE 8

17β-Hydroxy-17α-(E-2-iodovinyl)-4-estren-3-one 1.3 g of 3,3-ethylenedioxy-17α-(E-2-iodovinyl)-5 and 5(10)-estren-17β-ol are stirred with reflux in a mixture of 35 ml of methanol and 2.5 ml of water with 1.2 g of oxalic acid for 15 minutes. The reaction mixture is put in ice/water. The precipitated product is aspirated, dissolved in ethyl acetate, washed with water and dried with sodium sulfate. 1.0 g of 17β-Hydroxy-17α-(E-2-iodovinyl)-4-estren-3-one is obtained after recrystallization from acetone/hexane. Mp 130° C. (decomp.).

EXAMPLE 9

17α-(E-2-Bromovinyl)-17β-hydroxy-4-estren-3-one 1.3 g of 17α-(E-2-Bromovinyl)-3,3-ethylenedioxy-5 and 5(10)-estren-17β-ol, analogously to example 8, are converted to 17α-(E-2-Bromovinyl)-17β-hydroxy-4-estren-3-one. Yield: 830 mg, Mp 132° C. (Decomp.).

EXAMPLE 10

17β-Hydroxy-18-methyl-17α-(Z-2-tributylstannylvinyl)-4-estren-3-one 3 g of 17α-ethinyl-17β-hydroxy-18-methyl-4-estren-3-one, analogously to example 1, are reacted with tributyltin hydride. 1.9 g of 17β-hydroxy-18-methyl-17α-(Z-2-tributylstannylvinyl)-4-estren-3-one are obtained after chromatographing of the crude produce on silica gel with 0–10% ethyl acetate/hexane. Mp 120°–121° C.

EXAMPLE 11

17β-Hydroxy-17α-(Z-2-iodovinyl)-18-methyl-4-estren-3-one 1.0 g of 17β-hydroxy-18-methyl-17α-(Z-2-tributylstannylvinyl)-4-estren-3-one, analogously to example 2, are reacted with N-iodosuccinimide. 580 mg of 17β-hydroxy-17α-(Z-2-iodovinyl)-18-methyl-4-estren-3-one are obtained.

EXAMPLE 12

17α-(Z-2-Bromovinyl)-17β-hydroxy-18-methyl-4-estren-3-one 500 mg of 17β-hydroxy-18-methyl-17α-(Z-2-tributylstannylvinyl)-4-estren-3-one, analogously to example 3, are converted, with N-bromosuccinimide, to 17α-(Z-2-bromovinyl)-17β-hydroxy-18-methyl-4-estren-3-one. Yield: 310 mg

EXAMPLE 13

3,3-(2-2-Dimethyltrimethylenedioxy)-18-methyl-17α-(E-2-tributylstannylvinyl)-5 and 5(10),15-estradien-17β-ol 1.3 g of 3,3-(2,2-dimethyltrimethylenedioxy-18-methyl-5 and 5(10),15-estradien-17β-ol (U.S. Pat. No. 4,081,537), analogously to example 5, are converted to 3,3-(2,2-dimethyltrimethylenedioxy)-18-methyl-17α-(E-2-tributylstannylvninyl)-5 and 5(10),15-estradien-17β-ol. Yield: 890 mg as oil.

EXAMPLE 14

3,3-(2,2-dimethyltrimethylenedioxy)-17α-(E-2-iodovinyl)-18-methyl-5 and 5(10),15-estradien-17β-ol 730 mg of 3,3-(2-2-dimethyltrimethylenedioxy)-18-methyl-17α-(E-2-tributylstannylvinyl)-5 and 5(10),15-estradien-17β-ol, analogously to example 6, are reacted with N-iodosuccinimide. 430 mg of 3,3-(2,2-dimethyltrimethylenedioxy)-17α-(E-2-iodovinyl)-18-methyl-5 and 5(10)-estradien-17β-ol are isolated as oil.

EXAMPLE 15

17α-(E-2-Bromovinyl)-3,3-(2,2-dimethyltrimethylenedioxy)-18-methyl-5 and 5(10),15-estradien-17β-ol 520 mg of 3,3-(2,2-dimethyltrimethylenedioxy)-18-methyl-17α-(E-2-tributylstannylvinyl)-5 and 5(10),15-estradien-17β-ol, analogously to example 7, are converted to 17α-(E-2-bromovinyl)-3,3-(2,2-dimethyltrimethylenedioxy)-18-methyl-5 and 5(10),15-estradien-17β-ol. Yield: 270 mg as oil.

EXAMPLE 16

17β-Hydroxy-17α-(E-2-iodovinyl)-18-methyl-4,15-estradien-3-one 360 mg of 3,3-(2,2-dimethyltrimethylenedioxo)-17α-(E-2-iodovinyl)-18-methyl-5 and 5(10),15-estradien-17β-ol, analogously to example 8, are converted to 17β-Hydroxy-17α-(E-2-iodovinyl)-18-methyl-4,15-estradien-3-one. Yield: 210 mg.

EXAMPLE 17

17α-(E-2-Bromovinyl-17β-hydroxy-18-methyl-4,15-estradien-3-one 200 mg of 17α-(E-2-bromovinyl)-3,3-(2,2-dimethyltrimethylenedioxy)-18-methyl-5 and 5(10),15-estradien-17β-ol, analogously to example 8, are converted to 130 mg of 17α-(E-2-bromovinyl)-17β-hydroxy-18-methyl-4,15-estradien-3-one.

EXAMPLE 18

18-Methyl-11-methylene-17α-(Z-2-tributylstannylvinyl)-4-estren-17β-ol 2.5 g of 17α-ethinyl-18-methyl-11-methylene-4-estren-17β-ol (DT 2361120 (1974)), analogously to example 1, are reacted with tributyltin hydride. After chromatographing on silica gel with 0–5% ethyl acetate/hexane 1.7 g of 18-methyl-11-11-methylene-17α-(Z-2-tributylstannlyvinyl)-4-estren-17β-ol are obtained as oil.

EXAMPLE 19

17α-(Z-2-Iodovinyl)-18-methyl-11-methylene-4-estren-17β-ol 760 mg of 18-methyl-11-methylene-17α-(2-tributylstannylvinyl)-4-estren-17β-ol, analogously to example 2, are reacted with N-iodosuccinimide. 320 mg of 17α-(Z-2-Iodovinyl)-18-methyl-11-methylene-4-estren-17β-ol are obtained.

EXAMPLE 20

17α-(Z-2-Bromovinyl)-18-methyl-11-methylene-4-estren-17β-ol 630 mg of 18-methyl-11-methylene-17α-(Z-2-tributylstannylvinyl)-4-estren-17β-ol, analogously to example 3, are reacted with N-bromosuccinimide. 390 mg of 17α-(Z-2-bromovinyl)-18-methyl-11-methylene-4-estren-17β-ol are obtained.

EXAMPLE 21

17α-Ethinyl-3,3-(2,2-dimethyltrimethylenedioxy)-18-methyl-11-methylene-5-estren-17β-ol 3.2 g of 17α-ethinyl-17β-hydroxy-18-methyl-11-methylene-4-estren-3-one (DT 2361120 (1974)) in 40 ml methylene chloride are stirred at room temperature with 3 g of 2,2-dimethyl-1,3-propanediol, 4 ml of triethyl orthoformate and 400 mg of p-toluenesulfonic acid. After 3 hours, the solution is diluted with methylene chloride and washed with sodium bicarbonate solution and water one after the other. The crude product is chromatographed on silica gel with 0–15% acetone/hexane. 2.6 g of 17α-ethinyl-3,3-(2,2-dimethyltrimethylenedioxy)-18-methyl-11-methylene-5-estren-17β-ol are obtained. Mp 196.2° C.

EXAMPLE 22

3,3-(2,2-Dimethyltrimethylenedioxy)-18-methyl-11-methylene-17α-(E-2-Tributylstannylvinyl)-5-estren-17β-ol 1.4 g of 17α-ethinyl-3,3-(2,2-dimethyltrimethylenedioxy)-18-methyl-11-methylene-5-estren-17β-ol, analogously to example 5, are converted to 3,3-(2,2-Dimethyltrimethylenedioxy)-18-methyl-11-methylene-17α-(2-tri-n-butylstannylvinyl)-5-estren-17β-ol. After chromatographing of the crude product on silica gel with 0–10% ethyl acetate/hexane 1.1 g of 3,3-(2,2-dimethyl-trimethylenedioxy)-18-methyl-11-methylene-17α-(E-2-tributylstannylvinyl)-5-estren-17β-ol are obtained as oil.

EXAMPLE 23

3,3-(2,2-Dimethyltrimethylenedioxy)-17α-(E-2-iodovinyl)-18-methyl-11-methylene-5-estren-17β-ol 460 mg of 3,3-(2,2-dimethyltrimethylenedioxy)-18-methyl-11-methylene-17α-(E-2-tributylstannylvinyl)-5-estren-17β-ol, analogously to example 6, are reacted with N-iodosuccinimide. 280 mg of 3,3-(2,2-dimethyltrimethylenedioxy)-17α-(E-2-iodovinyl)-18-methyl-11-methylene-5-estren-17β-ol are obtained as oil.

EXAMPLE 24

17α-(E-2-Bromovinyl)-3,3-(2,3-dimethyltrimethylenedioxy)-18-methyl-11-methylene-5-estren-17β-ol 510 mg of 3,3-(2,2-dimethyltrimethylenedioxy)-18-methyl-11-methylene-17α-(E-2-tributylstannylvinyl)-5-estren-17β-ol, analogously to example 7, are reacted with N-bromosuccinimide. 300 mg of 17α-(E-2-bromovinyl)-3,3-(2,2-trimethylenodioxy)-18-methyl-11-methylene-5-estren-17β-ol are isolated as foam.

EXAMPLE 25

17β-Hydroxy-17α-(E-2-iodovinyl)-18-methyl-11-methylene-4-estren-3-one 210 mg of 3,3-(2,2-dimethyltrimethylenedioxy)-17α-(E-2-iodovinyl)-18-methyl-11-methylene-5-estren-17β-ol are reacted analogously to example 8. 130 mg of 17β-hydroxy-17α-(E-2-iodovinyl)-18-methyl-11-methylene-4-estren-3-one are obtained.

EXAMPLE 26

17α-(E-2-Bromovinyl)-17β-hydroxy-18-methyl-11-methylene-4-estren-3-one 250 mg of 17α-(E-2-bromovinyl)-3,3-(2,2-trimethylenedioxy)-18-methyl-11-methylene-5-estren-17β-ol, analogously to example 8, are converted to 17α-(E-2-bromovinyl)-17β-hydroxy-18-methyl-11-methylene-4-estren-3-one. Yield: 140 mg.

EXAMPLE 27

17β-Hydroxy-17α-(Z-2-tributylstannylvinyl)-4-androsten-3-one 4.5 g of 17α-ethinyl-17β-hydroxy-4-androstan-3-one, analogously to example 1, are reacted with tributyltin hydride. After chromatographing of the crude product on silica gel with 0–20% ethyl acetate/hexane, 2.6 g of 17β-hydroxy-17α-(Z-2-tributylstannylvinyl)-4-androstan-3-one are obtained as oil.

EXAMPLE 28

17β-Hydroxy-17α-(Z-2-iodovinyl)-4-androsten-3-one 1.4 g of 17β-Hydroxy-17α-(Z-2-tributylstannylvinyl)-4-androsten-3-one, analogously to example 2, are reacted with N-iodosuccinimide, whereby 710 mg of 17β-hydroxy-17α-(Z-2-iodovinyl)-4-androsten-3-one are obtained.

EXAMPLE 29

3,3-Ethylenedioxy-17β-tetrahydropyranyloxy-17α-(E-2-tributylstannylvinyl)-5-estrene 5.6 g of 17α-ethinyl-3,3-ethylenedioxy-17β-tetrahydroxypyranyloxy-5-estrene (DA-ES 1242607 (1967) are reacted analogously to example 5. After chromatographing of the crude product on silica gel with 0–10% ethyl acetate/hexane, 3.9 g of 3,3-ethylenedioxy-17β-tetrahydropyraryloxy-17α-(E-2-tributylstannylvinyl)-5-estrene are obtained as oil.

EXAMPLE 30

3,3-Ethylenedioxy-17α-(E-2-iodovinyl)-17β-tetrahydropyranyloxy-5-estrene 3.1 g of 3,3-ethylenedioxy-17β-tetrahydropyranyloxy-17α-(E-2-tributylstannylvinyl)-5-estrene, analogously to example 2, with N-iodosuccinimide is converted to 3,3-ethylenedioxy-(17α-(E-2-iodovinyl)-17β-tetrahydropyranyloxy-5-estrene. 1.9 g are obtained as oil.

EXAMPLE 31

17β-Hydroxy-17α-(E-2-iodovinyl)-4-estren-3-one

Analogously to example 8, 710 mg of 17β-hydroxy-17α-(E-2-iodovinyl)-4-estren-3-one are obtained from 1.6 g of 3,3-ethylendioxy-17α-(E-2-iodovinyl)-17β-tetrahydropyranyloxy-5-estrene. Mp 124.6° C.

EXAMPLE 32

17β-Acetoxy-3,3-ethylenedioxy-17α-(E-2-tributylstannylvinyl)-5 and 5(10)-estrene 6.3 g of 17β-acetoxy-3,3-ethylenedioxy-5 and 5(10)-estrene [tetrahedron 20, 2295 (1964)], analogously to example 5, are reacted with tributyltin hydride. After chromatographing of the crude product on silica gel with 0–15% ethyl acetate/hexane, 4.7 g of 17β-acetoxy-3,3-ethylenedioxy-17α-(E-2-tributylstannylvinyl)-5 and 5(10)-estreneals are obtained as oil.

EXAMPLE 33

17β-Acetoxy-3,3-ethylenedioxy-17α-(E-2-iodovinyl)-5 and 5(10)-estrene 3.6 g of 17β-acetoxy-3,3-ethylenedioxy-17α-(E-2-tributylstannylvinyl)-and 5(10)-estrene, analogously to example 6, are reacted with N-iodosuccinimide. 2.3 g of 17β-acetoxy-3,3-ethylene-dioxy-17α-(E-2-iodovinyl)-5 and 5(10)-estrene are obtained as foam.

EXAMPLE 34

17β-Acetoxy-17α-(E-2-iodovinyl)-4-estren-3-one 1.9 g of 17β-acetoxy-3,3-ethylenedioxy-17α-(E-2-iodovinyl)-5 and 5(10)-estrene are reacted analogously to example 8. 890 mg of 17β-acetoxy-17α-(E-2-iodovinyl)-4-estren-3-one are obtained.

EXAMPLE 35

17aβ-Hydroxy-17aα-(Z-2-tributylstannylvinyl)-D-homo-4-estren-3-one 7.3 g of 17aα-ethinyl-17aβ-hydroxy-D-homo-4-estren-3-one [U.S. Pat. No. 3,850,911 (1974)] are reacted analogously to example 1. After chromatographing on silica gel with 0–20% ethyl acetate/hexane, 4.2 g of 17aβ-hydroxy-17aα-(Z-2-tributylstannylvinyl)-D-homo-4-estren-3-one are obtained as foam.

EXAMPLE 36

17aβ-Hydroxy-17aα-(Z-2-iodovinyl)-D-homo-4-estren-3-one 800 mg of 17aβ-hydroxy-17aα-(Z-2-tributylstannylvinyl)-D-homo-4-estren-3-one are reacted with N-iodosuccinimide analogously to example 2. 210 mg of 17aβ-hydroxy-17aα-(Z-2-iodovinyl)-D-homo-4-estren-3-one are obtained.

EXAMPLE 37

3,3-(2,2-Dimethyltrimethylenedioxy)-18-methyl-15α,16α-methylene-17α-(E-2-tributylstannylvinyl)-5 and 5(10)-estren-17β-ol 5.8 g of 17α-ethyinyl-3,3-(2,2-dimethyltrimethylenedioxy)-18-methyl-15α,16α-methylene-5 and 5(10)-estren-17β-ol (U.S. Pat. No. 3,994,937) are reacted analogously to example 5. After chromatographing of the crude product on silica gel with 0–15% ethyl acetate/hexane, 3.9 g of 3,3-(2,2-dimethyltrimethylenedioxy-18-methyl-15α,16α-methylene-17α(E 2-tributylstannylvinyl)-5 and 5(10)-estrene-17β-ol are obtained as oil.

EXAMPLE 38

3,3-(2,2-Dimethyltrimethylenedioxy)-17α-(E-2-iodovinyl)-18-methyl-15α,16α-methylene-5 and 5(10)-estren-17β-ol 1.5 g of 3,3-(2,2-dimethyltrimethylenedioxy)-18-methyl-15α,16α-methylene-17α-(E-2-tributylstannylvinyl)-5 and 5(10)-estren-17β-ol are reacted with N-iodosuccinimide analogously to example 6. 830 mg of 3,3-(2,2 dimethyltrimethylenedioxy)-17α-(E-2-iodovinyl)-18-methyl-15α,16α-methylene-5 and 5(10)-estren-17β-ol are obtained as frothy product.

EXAMPLE 39

17α-(E-2-Bromovinyl)-3,3-(2,2-dimethyltrimethylenedioxy)-18-methyl-15α,16α-methylene-5 and 5(10)-estren-17β-ol 850 mg of 3,3-(2,2-dimethyltrimethylenedioxy)-18-methyl-15α,16α-methylene-17α-(E-2-tributylstannylvinyl)-5 and 5(10)-estrene-17β-ol, analogously to example 7, with N-bromosuccinimide are converted to 17α-(E-2-bromovinyl)-3,3-(2,2-dimethyl-trimethylendioxy)-18-methyl-15α,16α-methylene-5 and 5(10)-estrene-17β-ol. Yield: 410 mg as foam.

EXAMPLE 40

17β-Hydroxy-17α-(E-2-iodovinyl)-18-methyl-15α,16α-methylene-4-estrene-3-one

Analogously to example 8, 390 mg of 17β-hydroxy-17α(E2-iodovinyl)-18-methyl-15α,16α-methylene-4-estren-3-one are obtained as a frothy product from 650 mg of 3,3(2,2-dimethyltrimethylenedioxy)-17α-(E-2- iodovinyl)-18-methyl-15α,16α-methylene-5 and 5(10)-estren-17β-ol.

EXAMPLE 41

17α-(E-2-Bromovinyl)-17β-hydroxy-18-methyl-15α,16α-methylene-4-estren-3-one

Analogously to example 8, 130 mg 17α-(E-2-bromovinyl)-17β-hydroxy-18-methyl-15α,16α-methylene-4-estren-3-one are obtained as a foam from 300 mg of 17α-(E-2-bromovinyl)-3,3(2,2-dimethyltrimethylenedioxy)-18-methyl-15α,16α-methylene-5 and 5(10)-estren-17β-ol.

EXAMPLE 42

17β-Hydroxy-18-methyl-15β,16βmethylene-17α-(Z-2-tributylstannylvinyl)-4-estren-3-one 4.3 g of 17α-ethinyl-17β-hydroxy-18-methyl-15β,16β-methylene-4-estren-3-one (DT 1643050) are reacted with tributyltin hydride analogously to example 1. After chromatographing of the crude product on silica gel with 0–15% ethyl acetate/hexane 2.3 g of 17β-hydroxy-18-methyl-15β,16β-methylene-17α-(Z-2-tributylstannylvinyl)-4-estren-3-one are obtained as oil.

EXAMPLE 43

17β-Hydroxy-17α-(Z-2-iodovinyl)-18-methyl-15β,16β-methylene-4-estren-3-one 560 mg of 17β-hydroxy-18-methyl-15β,16β-methylene-17α-(Z-2-tributylstannylvinyl)-4-estren-3-one, analogously to example 2, are reacted with N-iodosuccinimide. 280 mg of 17β-hydroxy-17α-(Z-2-iodovinyl)-18-methyl-15β,16β-methylene-4-estren-3-one are obtained as foam.

EXAMPLE 44

17α-(Z-2-Bromovinyl)-17β-hydroxy-18-methyl-15β,16β-methylene-4-estren-3-one

Analogously to example 3, 110 mg of 17α-(Z-2-bromovinyl)-17β-hydroxy-18-methyl-15β,16β-methylene-4-estren-3-one are isolated as foam from 380 mg of 17β-hydroxy-18-methyl-15β,16β-methylene-17α-(Z-2-tributylstannylvinyl)-4-estren-3-one.

EXAMPLE 45

17β-Hydroxy-17α-(Z-2-[$^{131}$I]-iodovinyl)-4-estren-3-one

5 μg (0.11 μmol) of 17β-hydroxy-17α-(Z-2-iodovinyl)-4-estren-3-one are dissolved in 0.25 ml of acetone (by P$_2$O$_5$ distil.) and refluxed under inert gas in the presence of 370 MBq of sodium [$^{131}$I] iodide of the highest specific activity for one hour.

After cooling to ice bath temperature, 0.5 ml of methanol, 0.1 ml of water and 1 μg of sodium iodide are added. To remove the ions, the solution is passed through a mixed bed ion exchanger or separated in a TLC system of dioxane/ammonia/water. 4 μg of 17β-hydroxy-17α-(Z-2-[$^{131}$I]-iodovinyl-4-estren-3-one are obtained with about 50% radiochemical yield with a specific activity of 185 MBq/4 μg (19.5 GBq/μmol). The chemical and radiochemical identity of the compound is confirmed by Co chromatography on TLC plates and analogous retention times in HPLC. For diagnostic or therapeutic use, the solution is concentrated in vacuo, dissolved in ethanol/propylene glycol and then sterilized by filtering.

$^{124}$I, $^{125}$I and $^{132}$I compounds are obtained in an analogous way.

EXAMPLE 46

5 μg (0.013 μmol) of 17α-(Z-2-bromovinyl)-17β-hydroxy-4-estren-3-one are dissolved in 0.25 ml of diethylene glycol diethyl ether (dry) and heated to 120° C. under inert gas in the presence of 370 MBq of sodium [$^{125}$I] iodide (carrier-free) and 1 μg of copper sulfate for 3 hours.

After cooling to ice bath temperature, 0.25 ml of methanol, 0.1 ml of water and 1 g of sodium iodide are added. To remove the ions, the solution is passed through a mixed bed ion exchanger. 2 μg of 17β-hydroxy-17α-(Z-2-[$^{125}$I]-iodovinyl)-4-estren-3-one are obtained with a specific activity that corresponds to the sodium [$^{125}$I] iodide used. Therefore it is in the order of magnitude of 80.29 GBq/μmol. The resulting 17β-hydroxy-17α-(Z-2-iodovinyl)-4-estren-3-one, carrier-free tagged with $^{125}$I, is separated from the initial product by silica gel chromatography in a low-pressure column in a hexane/acetone system (acetone 10→30%).

A product suitable for diagnostic purposes is obtained after concentration, absorption in ethanol/propylene glycol.

EXAMPLE 47

As described for example 45, 50 μg of (0.13 μmol) of 17β-hydroxy-17α-(Z-2-bromovinyl)-4-estren-3-one are treated with sodium [$^{82}$Br] bromide (carrier-free). After analogous working up, specifically highly tagged 17β-hydroxy-17α-(Z-2-bromovinyl)-4-estren-3-one is obtained.

The $^{77}$Br, $^{80m}$Br, $^{80}$Br tagged compound is obtained in a corresponding way.

EXAMPLE 48

50 μl of Na$^{125}$I, containing 185 MBq$^{125}$I, as aqueous neutral solution, are added to 500 μg of 17β-hydroxy-17α-(Z-2-tributylstannylvinyl)-4-estren-3-one in 250 μl of methyl ethyl ketone at room temperature. It is allowed to stand for 5 minutes at room temperature, the resulting materials are separated on an analytical HPTLC plate and the radioactive zone is eluted. The eluate is separated with a semipreparative HPLC column with radioactivity monitor. 1 mCi of pure 17β-hydroxy-17α-(Z-2-$^{125}$iodovinyl)-4-estren-3-one in methanolic aqueous solution is obtained. The radioactive tagging is carrier-free. The specific activity corresponds to that of the radioactive iodine used.

Analogously as for $^{125}$iodine described, the compound is also obtained tagged with $^{123}$iodine, $^{131}$iodine and $^{132}$iodine, as well as with $^{77}$bromine, $^{80m}$bromine and $^{82}$bromine.

EXAMPLE 49

50 μof Na$^{125}$I, containing 185 MBq$^{125}$I, as aqueous neutral solution, are added to 500 μg of 17β-hydroxy-17α-(Z-2-tributylstannylvinyl)-18-methyl-4-estren-3-one in 250 μl of methyl ethyl ketone at room temperature. It is allowed to stand for 5 min at room temperature, the resulting materials are separated on an analytical HPTLC plate and the radioactive zone eluted. The eluate is separated with a semipreparative HPLC column apparatus with radioactive monitor. 1 mCi of pure 17β-hydroxy-17α-(Z-2-$^{125}$iodovinyl)-18-methyl-4-estren-3-one in methanolic aqueous solution is obtained. The radioactive tagging is carrier-free. The specific activity corresponds to that of the radioactive iodine used.

Analogously as for $^{125}$iodine described, the compound is also obtained tagged with $^{123}$iodie, $^{131}$iodine and $^{132}$iodine, as well as with $^{77}$bromine, $^{80m}$bromine and $^{82}$bromine.

EXAMPLE 50

3,3-Ethylenedioxy-17α-(E-2-tributylstannylvinyl)-5(10),9(11)-17β-ol 5.0 g of 17α-ethinyl-3,3-ethylenedioxy-5(10),9(11)-estradien-17β-ol are reacted analogously to example 5. 5.9 g of 3,3-Ethylene-dioxy-17α-(E-2-tributylstannylvinyl)-5(10),9(11)-estradien-17β-ol are obtained as oil.

EXAMPLE 51

3,3-Ethylenedioxy-17α-(E-2-iodovinyl)-5(10),9(11)-estradien-17β-ol 2.0 g of 3,3-ethylenedioxy-17α-(E-2-tributylstannylvinyl)-5(10),9(11)-estradien-17β-ol are reacted analogously to example 6. 1.4 g 3,3-ethylenedioxy-17α-(E-2-iodovinyl)-5(10),9(11)-estradien-17β-ol are obtained as foam.

EXAMPLE 52

17α-(E-2-Bromovinyl)-3,3-ethylenedioxy-5(10),9(11)-estradien-17β-ol 2.0 g of 3,3-ethylendioxy-17α-(E-2-tributylstannylvinyl)-5(10),9(11)-estradien-17β-ol are reacted analogously to example 7. 1.8 g of 17α-(E-2-bromovinyl)-3,3-ethylendioxy-5(10),9(11)-estradien-17β-ol are isolated as oil.

EXAMPLE 53

17β-Hydroxy-17α-(E-2-iodovinyl)-4,9-estradien-3-one 1.3 g of 3,3-ethylenedioxy-17α-(E-2-iodovinyl)-5(10),9(11)-estradien-17β-ol are reacted analogously to example 8. 650 mg of 17β-Hydroxy-17α-(E-2-iodovinyl)-4,9-estradien-3-one are obtained as foam.

EXAMPLE 54

17α-(E-2-Bromovinyl)-17-hydroxy-4,9-estradien-3-one 1.0 g of 17α-(E-2-bromovinyl)-3,3-ethylenedioxy-5(10),9(11)-estradien-17β-ol are reacted analogously to example 8. 600 mg of 17α-(E-2-bromovinyl)-17β-hydroxy-4,9-estradien-3-one are obtained. Mp 112° C. (decomposition).

EXAMPLE 55

3,3-Ethylenedioxy-17α-(Z-2-tributylstannylvinyl)-5(10),9(11)-estradien-17β-ol 7.0 g of 17α-ethinyl-3,3-ethylenedioxy-5(10),9(11)-estradien-17β-ol are stirred in 30 ml of hexamethylphosphoric triamide and 30 ml of tributyltin hydride for 6 hours at 70° C. It is diluted with ethyl acetate, washed several times with water and dried with sodium sulfate. The crude product is chromatographed with toluene-ethyl acetate on silica gel. 4.2 g of 3,3-ethylenedioxy-17α-(Z-2-tributylstannylvinyl)-5(10),9(11)-estradien-17β-ol are isolated as oil.

EXAMPLE 56

3,3-Ethylenedioxy-17α-(Z-2-iodovinyl)-5(10),9(11)-estradien-17β-ol 1.5 g of 3,3-ethylenedioxy-17α-(Z-2-tributylstannylvinyl)-5(10),9(11)-estradien-17β-ol are reacted analogously to example 2. 650 mg of 3,3-ethylenedioxy-17α-(Z-2-iodovinyl)-5(10),9(11)-estradien-17β-ol are isolated as foam.

EXAMPLE 57

17α-(Z-2-Bromovinyl)-3,3-ethylenedioxy-5(10),9(11)-estradien-17β-ol 1.2 g of 3,3-ethylenedioxy-17α-(Z-2-tributylstannylvinyl)-5(10),9(11)-estradien-17β-ol are reacted analogously to example 3. 480 mg of 17α-(Z-2-bromovinyl)-3,3-ethylenedioxy-5(10),9(11)-estradien-17β-ol are obtained as foam.

EXAMPLE 58

17β-Hydroxy-17α-(Z-2-iodovinyl)-4,9-estradien-3-one 500 mg of 3,3-ethylendioxy-17α-(Z-2-iodovinyl)-5(10),9(11)-estradien-17β-ol are reacted analogously to example 8. 280 mg of 17β-hydroxy-17α-(Z-2-iodovinyl)-4,9-estradien-3-one are obtained. Mp a98° C. (decomposition).

EXAMPLE 59

17α(Z-2-Bromovinyl)-17β-hydroxy-4,9-estradien-3-one 350 mg of 17α-(Z-2-bromovinyl)-3,3-ethylenedioxy-5(10),9(11)-estradien-17β-ol are reacted analogously to example 8. 120 mg of 17α-(Z-2-bromovinyl)-17β-hydroxy-4,9-estradien-3-one are obtained as foam.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An estrane of the formula

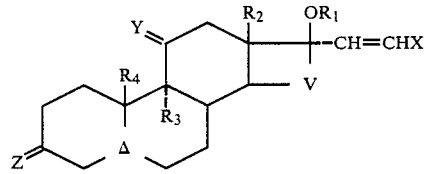

wherein
  X is bromo, iodo, triphenyltin or tri-($C_{1-6}$)alkyltin;
  Y is two hydrogen atoms or methylene;
  Z is two hydrogen atoms or oxo;
  V is vinylene, cyclopropylene or 1,3-propylene;
  $R_1$ is H, a $C_{1-8}$-hydrocarbon radical, or a $C_{1-8}$-hydrocarbon radical interrupted by an oxa atom or substitued by oxo;
  $R_2$ is methyl or ethyl;
  $R_3$ and $R_4$ together form a carbon-carbon bond, or $R_3$ is H and $R_4$ is H or methyl; and
  Δ symbolizes a 4(5) double bond.

2. A compound of claim 1 wherein X is a radioactive bromine isotope or a radioactive iodine isotope.

3. 17α-(2-Bromovinyl)-17β-hydroxy-18-methyl-4,15-estradien-3-one, a compound of claim 1.

4. 17β-Hydroxy-17α-(2-iodovinyl)-18-methyl-4,15-estradien-3-one, a compound of claim 1.

5. 17aα-Hydroxy-17aα-iodovinyl-D-homo-4-estren-3-one, a compound of claim 1.

6. 17α-(2-Bromovinyl)-17β-hydroxy-18-methyl-15α,16α-methylene-4-estren-3-one, a compound of claim 1.

7. 17β-Hydroxy-17α-iodovinyl-18-methyl-15α,16α-methylene-4-estren-3-one, a compound of claim 1.

8. 17α-(2-Bromovinyl)-17β-hydroxy-18-methyl-15β,16β-methylene-4-estren-3-one, a compound of claim 1.

9. 17β-Hydroxy-17α-iodovinyl-18-methyl-15β,16β-methylene-4-estren-3-one, a compound of claim 1.

10. An estrane of the formula

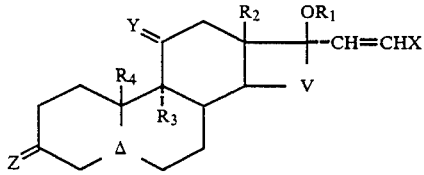

wherein
X is bromo, iodo, triphenyltin or tri-($C_{1-6}$)alkyltin;
Y is methylene;
Z is two hydrogen atoms or oxo;
V is ethylene, vinylene, cyclopropylene or 1,3-propylene;
$R_1$ is H, a $C_{1-8}$-hydrocarbon radical, or a $C_{1-8}$-hydrocarbon radical interrupted by an oxa atom or substitued by oxo;
$R_2$ is methyl or ethyl;
12$R_3$ and $R_4$ together form a carbon-carbon bond, or $R_3$ is H and $R_4$ is H or methyl; and
Δ symbolizes a 4(5) double bond.

11. A compound of claim 10 wherein X is a radioactive bromine isotope or a radioactive iodine isotope.

12. 17α-(2-Bromovinyl)-17β-hydroxy-18-methyl-11-methylene-4-estren-3-one, a compound of claim 10.

13. 17β-Hydroxy-17α-(2-iodovinyl)-18-methyl-11-methylene-4-estren-3-one, a compound of claim 10.

14. An estrane of the formula

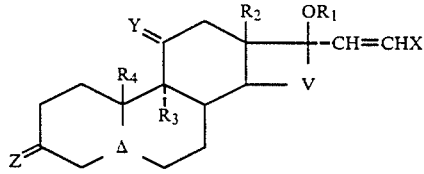

wherein
X is bromo, iodo, triphenyltin or tri-($C_{1-6}$)alkyltin;
Y is a hydrogen atom and, together with $R_3$, forms a 9(11) double bond;
Z is $C_{2-6}$-alkylenedioxy;
V is ethylene, vinylene, cyclopropylene or 1,3-propylene;
$R_1$ is H, a $C_{1-8}$-hydrocarbon radical, or a $C_{1-8}$-hydrocarbon radical interrupted by an oxa atom or substitued by oxo;
$R_2$ is methyl or ethyl;
$R_3$ is H; and
Δ symbolizes a 5(10) double bond.

15. A compound of claim 14 wherein X is a radioactive bromine isotope or a radioactive iodine isotope.

16. 3,3-Ethylenedioxy-17α-(2-tributylstannyl)-5(10),9(11)-estradien-17β-ol, a compound of claim 14.

17. 3,3-Ethylenedioxy-17α-(2-iodovinyl)-5(10),9(11)-estradien-17β-ol, a compound of claim 14.

18. 17α-(2-bromovinyl)-3,3-ethylenedioxy-5(10),9(11)-estradien-17β-ol, a compound of claim 14.

19. An estrane of the formula

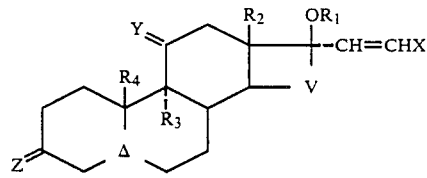

wherein
X is bromo, iodo, triphenyltin or tri-($C_{1-6}$)alkyltin;
Y is two hydrogen atoms or methylene;
Z is two hydrogen atoms or oxo;
V is ethylene, vinylene, cyclopropylene or 1,3-propylene;
$R_1$ is H;
$R_2$ is methyl or ethyl;
$R_3$ and $R_4$ together form a 9(10) carbon-carbon bond; and
Δ symbolizes a 4(5) double bond.

20. A compound of claim 19 wherein X is a radioactive bromine isotope or a radioactive iodine isotope.

21. 17β-Hydroxy-17α-(2-iodovinyl)-4,9-estradien-3-one, a compound of claim 19.

22. 17α-(2-Bromovinyl)-17β-hydroxy-4,9-estradien-3-one, a compound of claim 19.

23. A pharmaceutical composition comprising a gestagenically effective amount of a compound of claim 1 and a pharmaceutically acceptable carrier.

24. A composition of claim 23 which is a diagnostic composition wherein X is a radioactive Br or I isotope.

25. A pharmaceutical composition comprising a gestagenically effective amount of a compound of claim 10 and a pharmaceutically acceptable carrier.

26. A composition of claim 25 which is a diagnostic composition wherein X is a radioactive Br or I isotope.

27. A pharmaceutical composition comprising a gestagenically effective amount of a compound of claim 14 and a pharmaceutically acceptable carrier.

28. A composition of claim 27 which is a diagnostic composition wherein X is a radioactive Br or I isotope.

29. A pharmaceutical composition comprising a gestagenically effective amount of a compound of claim 19 and a pharmaceutically acceptable carrier.

30. A composition of claim 29 which is a diagnostic composition wherein X is a radioactive Br or I isotope.

31. In a method of visualizing an organ of a patient comprising administering to the patient an effective amount of a radioactively labelled compound which binds to that organ, and then scanning the organ by a technique which is responsive to radioactivity, the improvement wherein the compound is one of claim 2.

32. In a method of visualizing an organ of a patient comprising administering to the patient an effective amount of a radioactively labelled compound which binds to that organ, and then scanning the organ by a technique which is responsive to radioactivity, the improvement wherein the compound is one of claim 11.

33. In a method of visualizing an organ of a patient comprising administering to the patient an effective amount of a radioactively labelled compound which binds to that organ, and then scanning the organ by a technique which is responsive to radioactivity, the improvement wherein the compound is one of claim 15.

34. In a method of visualizing an organ of a patient comprising administering to the patient an effective amount of a radioactively labelled compound which binds to that organ, and then scanning the organ by a technique which is responsive to radioactivity, the improvement wherein the compound is one of claim 20.

35. In a method of performing an in vitro assay for the determination of progestagen receptors in a tissue sample comprising contacting the tissue sample with a radioactively labelled compound which binds to progestagen receptors, and then scanning the sample by a technique which is responsive to radioactivity, the improvement wherein the compound is one of claim 2.

36. In a method of performing an in vitro assay for the determination of progestagen receptors in a tissue sample comprising contacting the tissue sample with a radioactively labelled compound which binds to progestagen receptors, and then scanning the sample by a technique which is responsive to radioactivity, the improvement wherein the compound is one of claim 11.

37. In a method of performing an in vitro assay for the determination of progestagen receptors in a tissue sample comprising contacting the tissue sample with a radioactively labelled compound which binds to progestagen receptors, and then scanning the sample by a technique which is responsive to radioactivity, the improvement wherein the compound is one of claim 15.

38. In a method of performing an in vitro assay for the determination of progestagen receptors in a tissue sample comprising contacting the tissue sample with a radioactively labelled compound which binds to progestagen receptors, and then scanning the sample by a technique which is responsive to radioactivity, the improvement wherein the compound is one of claim 20.

* * * * *